United States Patent
Harper et al.

(10) Patent No.: US 10,541,529 B2
(45) Date of Patent: Jan. 21, 2020

(54) METHODS, APPARATUSES AND SYSTEMS FOR SENSING EXPOSURE OF ELECTRONIC DEVICES TO MOISTURE

(71) Applicant: HZO, Inc., Draper, UT (US)

(72) Inventors: Marcellus Harper, Kaysville, UT (US); Jason Maynard, Salt Lake City, UT (US); Blake Stevens, Morristown, NJ (US); Max Sorenson, Herriman, UT (US)

(73) Assignee: HZO, Inc., Morrisville, NC (US)

( * ) Notice: Subject to any disclaimer, the term of this patent is extended or adjusted under 35 U.S.C. 154(b) by 810 days.

(21) Appl. No.: 14/868,825

(22) Filed: Sep. 29, 2015

(65) Prior Publication Data

US 2016/0020599 A1    Jan. 21, 2016

Related U.S. Application Data

(63) Continuation of application No. 14/448,541, filed on Jul. 31, 2014, now Pat. No. 9,146,207, which is a (Continued)

(51) Int. Cl.
*H02H 5/08* (2006.01)
*G01N 27/22* (2006.01)
(Continued)

(52) U.S. Cl.
CPC .............. *H02H 5/083* (2013.01); *G01N 27/02* (2013.01); *G01N 27/023* (2013.01);
(Continued)

(58) Field of Classification Search
CPC .... G01N 27/02; G01N 27/023; G01N 27/223; G01R 27/2605; G01R 27/2611;
(Continued)

(56) References Cited

U.S. PATENT DOCUMENTS 3,898,547 A   8/1975   Poole
4,631,250 A   12/1986  Hayashi
(Continued)

FOREIGN PATENT DOCUMENTS

CN    1567554 A      1/2005
CN    102150480 A    8/2011
(Continued)

OTHER PUBLICATIONS pctechguide.com, Principles of CPU architecture—logic gates, MOSFETS, and voltage. www.pctechguide.com. Wayback dated verfied to Aug. 2011. (Year: 2011).*
(Continued)

*Primary Examiner* — Patrick Assouad
*Assistant Examiner* — Sean Curtis
(74) *Attorney, Agent, or Firm* — Intellectual Strategies

(57) ABSTRACT

Systems, devices and methods for sensing moisture within an electronic device are disclosed. A device may include a housing and a display defining and exterior of an electronic device and an interior of the electronic device. Further, the device may include an integrated circuit (IC) within the electronic device and comprising a control element. The device may also include a moisture sensor such as an inductive sensor, a capacitance sensor, or both. The moisture sensor, which may be part of the IC, together with the control element may sense moisture within the electronic device.

17 Claims, 6 Drawing Sheets

Related U.S. Application Data continuation-in-part of application No. 13/734,779, filed on Jan. 4, 2013, now Pat. No. 9,071,046, and a continuation-in-part of application No. 14/320,799, filed on Jul. 1, 2014, now Pat. No. 9,157,880, which is a continuation of application No. 14/150,534, filed on Jan. 8, 2014, now Pat. No. 8,773,271.

(60) Provisional application No. 61/584,933, filed on Jan. 10, 2012, provisional application No. 61/750,328, filed on Jan. 8, 2013.

(51) Int. Cl.
| | |
|---|---|
| *G01R 27/26* | (2006.01) |
| *G06F 1/16* | (2006.01) |
| *G01N 27/02* | (2006.01) |
| *G01R 35/00* | (2006.01) |
| *H05B 1/02* | (2006.01) |
| *G06F 1/28* | (2006.01) |

(52) U.S. Cl.
CPC ....... *G01N 27/223* (2013.01); *G01R 27/2605* (2013.01); *G01R 27/2611* (2013.01); *G01R 35/005* (2013.01); *G06F 1/1656* (2013.01); *G06F 1/28* (2013.01); *H05B 1/02* (2013.01)

(58) Field of Classification Search
CPC .... G01R 35/005; H02H 5/083; G06F 1/1656; G06F 1/28; H05B 1/02
USPC .............................. 324/207.15, 445, 634, 664
See application file for complete search history.

(56) References Cited

U.S. PATENT DOCUMENTS

| | | | |
|---|---|---|---|
| 4,994,726 A | 2/1991 | Tamura et al. | |
| 5,184,427 A | 2/1993 | Armstrong | |
| 5,291,118 A | 3/1994 | Kojima | |
| 5,760,694 A * | 6/1998 | Nissim | A61F 13/42 |
| | | | 128/885 |
| 5,818,340 A * | 10/1998 | Yankielun | E04D 13/006 |
| | | | 340/602 |
| 5,865,635 A | 2/1999 | Hsiang et al. | |
| 5,999,384 A | 12/1999 | Chen et al. | |
| 6,052,287 A * | 4/2000 | Palmer | H01L 23/49827 |
| | | | 174/255 |
| 6,061,261 A | 5/2000 | Chen et al. | |
| 6,138,349 A | 10/2000 | Vinciarelli et al. | |
| 6,157,303 A * | 12/2000 | Bodie | B63C 9/0005 |
| | | | 340/539.1 |
| 6,157,765 A * | 12/2000 | Bruce | G02B 6/10 |
| | | | 372/6 |
| 6,319,827 B1 * | 11/2001 | Kowalski | G06K 19/07747 |
| | | | 257/678 |
| 6,445,086 B1 | 9/2002 | Houston | |
| 6,495,892 B2 * | 12/2002 | Goodman | G01N 33/0031 |
| | | | 257/414 |
| 6,526,807 B1 * | 3/2003 | Doumit | G01M 3/04 |
| | | | 340/605 |
| 6,552,888 B2 | 4/2003 | Weinberger | |
| 7,050,837 B2 * | 5/2006 | Menz | H04M 1/18 |
| | | | 455/572 |
| 7,061,061 B2 * | 6/2006 | Goodman | G01N 27/128 |
| | | | 257/414 |
| 7,332,834 B2 | 2/2008 | Lee | |
| 7,411,317 B2 | 8/2008 | Liu | |
| 7,446,432 B2 | 11/2008 | Cha | |
| 7,481,107 B2 * | 1/2009 | Itakura | G01N 27/223 |
| | | | 73/335.02 |
| 7,498,802 B2 * | 3/2009 | Takahata | G01D 5/2066 |
| | | | 324/207.15 |
| 7,550,310 B2 * | 6/2009 | Goodman | G01N 27/128 |
| | | | 438/49 |
| 7,550,873 B2 | 6/2009 | Jiang et al. | |
| 7,795,759 B2 | 9/2010 | DuBose et al. | |
| 7,800,252 B2 | 9/2010 | DuBose et al. | |
| 7,880,591 B2 * | 2/2011 | Johnson | G06F 21/554 |
| | | | 340/11.1 |
| 7,897,881 B2 | 3/2011 | Kaspar et al. | |
| 7,960,944 B2 | 6/2011 | Hoffman et al. | |
| 7,977,823 B2 | 7/2011 | DuBose et al. | |
| 7,978,447 B2 | 7/2011 | Baxter | |
| 7,990,670 B2 | 8/2011 | Chen | |
| 8,000,858 B2 | 8/2011 | Tonegawa et al. | |
| 8,030,890 B2 | 10/2011 | Hyatt | |
| 8,063,765 B2 * | 11/2011 | Johnson | G06F 21/554 |
| | | | 307/116 |
| 8,169,196 B2 | 5/2012 | Vantu et al. | |
| 8,198,757 B2 | 6/2012 | Brink et al. | |
| 8,259,221 B1 | 9/2012 | Kaplan et al. | |
| 8,368,350 B2 | 2/2013 | Iwanaga et al. | |
| 8,374,729 B2 | 2/2013 | Chapel et al. | |
| 8,416,542 B2 * | 4/2013 | Nakamura | G01M 3/16 |
| | | | 361/42 |
| 8,456,178 B2 * | 6/2013 | Wang | G01N 27/023 |
| | | | 324/654 |
| 8,519,566 B2 | 8/2013 | Recker et al. | |
| 8,542,023 B2 * | 9/2013 | Potyrailo | G01N 27/02 |
| | | | 324/652 |
| 8,542,024 B2 * | 9/2013 | Potyrailo | G01N 27/02 |
| | | | 324/652 |
| 8,683,861 B2 * | 4/2014 | Humbert | G01N 17/04 |
| | | | 422/53 |
| 8,698,641 B2 * | 4/2014 | Abraham | A61F 13/42 |
| | | | 340/539.1 |
| 8,773,271 B1 * | 7/2014 | Stevens | H03K 17/94 |
| | | | 340/604 |
| 8,836,349 B2 * | 9/2014 | Rocznik | G01R 27/2605 |
| | | | 324/679 |
| 8,886,971 B2 * | 11/2014 | Chuang | G06F 1/26 |
| | | | 713/300 |
| 9,027,400 B2 * | 5/2015 | Le Neel | G01N 27/223 |
| | | | 73/335.04 |
| 9,071,046 B2 * | 6/2015 | Stevens | H02H 5/00 |
| 9,146,207 B2 * | 9/2015 | Harper | G06F 1/1656 |
| 9,157,880 B2 * | 10/2015 | Stevens | H03K 17/94 |
| 9,278,033 B2 * | 3/2016 | Abraham | A61F 13/42 |
| 9,488,565 B2 * | 11/2016 | Zielinski | G01N 19/10 |
| 9,583,257 B2 * | 2/2017 | Blomqvist | H01F 29/00 |
| 9,589,686 B2 * | 3/2017 | Potyrailo | G21C 17/022 |
| 9,752,999 B2 * | 9/2017 | Kalinichev | G01N 27/048 |
| 9,800,713 B2 * | 10/2017 | Dempster | H04M 1/72569 |
| 9,823,286 B2 * | 11/2017 | Connell | G01R 31/00 |
| 9,831,661 B2 * | 11/2017 | Chung | H02H 5/083 |
| 9,939,398 B2 * | 4/2018 | Dempster | G01N 27/048 |
| 10,008,373 B1 * | 6/2018 | Carr | G01R 33/0035 |
| 2002/0005580 A1 * | 1/2002 | Goodman | G01N 33/0031 |
| | | | 257/734 |
| 2002/0074970 A1 | 6/2002 | Kawashima | |
| 2002/0097546 A1 | 7/2002 | Weinberger | |
| 2002/0101695 A1 | 8/2002 | Saksa | |
| 2002/0112945 A1 | 8/2002 | Lawson et al. | |
| 2002/0170897 A1 | 11/2002 | Hall | |
| 2002/0187260 A1 | 12/2002 | Sheppard et al. | |
| 2003/0136960 A1 * | 7/2003 | Goodman | G01N 27/128 |
| | | | 257/40 |
| 2004/0130288 A1 | 7/2004 | Souther et al. | |
| 2004/0257037 A1 | 12/2004 | Hartung et al. | |
| 2005/0179140 A1 | 8/2005 | Goodner et al. | |
| 2005/0267698 A1 | 12/2005 | Gordon | |
| 2006/0036885 A1 | 2/2006 | Hsieh | |
| 2006/0125434 A1 | 6/2006 | Frohne et al. | |
| 2006/0181241 A1 | 8/2006 | Veselic | |
| 2006/0186901 A1 * | 8/2006 | Itakura | G01N 27/223 |
| | | | 324/689 |
| 2006/0201232 A1 * | 9/2006 | Itakura | G01N 27/223 |
| | | | 73/1.02 |
| 2006/0208254 A1 * | 9/2006 | Goodman | G01N 27/128 |
| | | | 257/40 |
| 2006/0208914 A1 * | 9/2006 | Liu | G01N 27/048 |
| | | | 340/620 |

(56) References Cited

U.S. PATENT DOCUMENTS

| | | |
|---|---|---|
| 2006/0264153 A1 | 11/2006 | Jaubertie |
| 2007/0038334 A1 | 2/2007 | Chou et al. |
| 2007/0043725 A1* | 2/2007 | Hotelling ............... G06F 3/016 |
| 2007/0046106 A1 | 3/2007 | Shintomi |
| 2007/0062027 A1* | 3/2007 | Ripamonti ......... H01F 17/0033 |
| | | 29/602.1 |
| 2007/0169535 A1* | 7/2007 | Itakura ................ G01N 27/223 |
| | | 73/1.06 |
| 2007/0182368 A1 | 8/2007 | Yang |
| 2007/0254697 A1* | 11/2007 | Sugio ............... H04M 1/72538 |
| | | 455/556.2 |
| 2008/0088462 A1* | 4/2008 | Breed .................... B60C 11/24 |
| | | 340/573.1 |
| 2008/0164768 A1 | 7/2008 | Litwack |
| 2008/0204128 A1 | 8/2008 | Brenner et al. |
| 2008/0204218 A1 | 8/2008 | Tupman et al. |
| 2008/0283180 A1 | 11/2008 | Bachman et al. |
| 2009/0001938 A1 | 1/2009 | Vantu et al. |
| 2009/0015372 A1 | 1/2009 | Kady |
| 2009/0119520 A1 | 5/2009 | Yoshioka et al. |
| 2009/0122633 A1 | 5/2009 | Roewer |
| 2009/0124990 A1* | 5/2009 | Feldkamp ............... A61F 13/42 |
| | | 604/361 |
| 2009/0129128 A1 | 5/2009 | Hirahara |
| 2009/0160404 A1 | 6/2009 | Iwai |
| 2009/0207031 A1* | 8/2009 | Barth .................. G08B 21/182 |
| | | 340/605 |
| 2009/0263581 A1 | 10/2009 | Martin, III et al. |
| 2009/0263641 A1 | 10/2009 | Martin, III et al. |
| 2010/0033883 A1 | 2/2010 | Simon |
| 2010/0159699 A1 | 6/2010 | Takahashi |
| 2010/0176956 A1* | 7/2010 | Moerschell ............... E04H 4/06 |
| | | 340/573.6 |
| 2010/0178885 A1* | 7/2010 | Senda .................... H04W 52/20 |
| | | 455/115.2 |
| 2010/0192688 A1* | 8/2010 | Humbert ................ G01N 17/04 |
| | | 73/335.03 |
| 2010/0270860 A1 | 10/2010 | Kamaga |
| 2010/0302757 A1 | 12/2010 | Bennett, Jr. |
| 2010/0304091 A1 | 12/2010 | Wang |
| 2010/0307238 A1* | 12/2010 | Van Popta ........... G01N 27/225 |
| | | 73/335.04 |
| 2011/0064737 A1 | 3/2011 | Agus |
| 2011/0095884 A1* | 4/2011 | Xu ........................... A61F 13/42 |
| | | 340/539.11 |
| 2011/0104940 A1 | 5/2011 | Rabu et al. |
| 2011/0121985 A1* | 5/2011 | Yamamoto ............ G06F 1/1615 |
| | | 340/650 |
| 2011/0131003 A1 | 6/2011 | Tusvik |
| 2011/0140717 A1* | 6/2011 | Wang .................... G01N 27/023 |
| | | 324/654 |
| 2011/0141205 A1 | 6/2011 | Gemer et al. |
| 2011/0147174 A1 | 6/2011 | Chuang |
| 2011/0161694 A1 | 6/2011 | Fujiwara |
| 2011/0208993 A1 | 8/2011 | Samoilova et al. |
| 2011/0253429 A1 | 10/2011 | Humphries et al. |
| 2011/0262740 A1 | 10/2011 | Martin, III et al. |
| 2011/0264398 A1 | 10/2011 | Niewczas et al. |
| 2011/0279931 A1* | 11/2011 | Nakamura ............... G01M 3/16 |
| | | 361/42 |
| 2012/0116683 A1* | 5/2012 | Potyrailo ............... G01N 27/02 |
| | | 702/19 |
| 2012/0161787 A1* | 6/2012 | Potyrailo ............... G01N 27/02 |
| | | 324/652 |
| 2012/0166095 A1* | 6/2012 | Potyrailo ........... G01N 27/3278 |
| | | 702/23 |
| 2012/0194952 A1 | 8/2012 | Crucs |
| 2012/0231841 A1* | 9/2012 | Niederberger .......... H04M 1/21 |
| | | 455/556.1 |
| 2012/0286949 A1* | 11/2012 | Worthington ............. F16P 3/14 |
| | | 340/539.1 |
| 2013/0111100 A1 | 5/2013 | Ghosh et al. |
| 2013/0131618 A1* | 5/2013 | Abraham ................ A61F 13/42 |
| | | 604/361 |
| 2013/0139587 A1* | 6/2013 | Le Neel ................ G01N 27/223 |
| | | 73/335.04 |
| 2013/0162198 A1 | 6/2013 | Yokota et al. |
| 2013/0174410 A1 | 7/2013 | Stevens et al. |
| 2013/0176691 A1 | 7/2013 | Stevens et al. |
| 2013/0176700 A1 | 7/2013 | Stevens et al. |
| 2013/0182360 A1* | 7/2013 | Stevens ..................... H02H 5/00 |
| | | 361/71 |
| 2013/0225237 A1* | 8/2013 | Minami ............ H04W 52/0245 |
| | | 455/556.1 |
| 2013/0286567 A1 | 10/2013 | Sorenson et al. |
| 2013/0290764 A1 | 10/2013 | Taki |
| 2013/0295782 A1 | 11/2013 | Goel |
| 2013/0335898 A1 | 12/2013 | Stevens et al. |
| 2014/0075212 A1 | 3/2014 | Urbina et al. |
| 2015/0016000 A1* | 1/2015 | Quirk ..................... H02H 5/083 |
| | | 361/78 |
| 2016/0020599 A1* | 1/2016 | Harper .................. G06F 1/1656 |
| | | 324/664 |
| 2017/0328855 A1* | 11/2017 | Cobianu ............. G01N 27/223 |
| 2018/0356360 A1* | 12/2018 | Mitsunaka ........... G01N 27/228 |
| 2019/0025235 A1* | 1/2019 | Mitsunaka ............. G01N 22/04 |

FOREIGN PATENT DOCUMENTS

| | | |
|---|---|---|
| CN | 202049235 U | 11/2011 |
| CN | 102655949 A | 9/2012 |
| DE | 10203815 C1 | 4/2003 |
| EP | 1621874 A1 | 2/2006 |
| JP | 62-187258 A | 8/1987 |
| JP | 01-170311 A | 7/1989 |
| JP | 07-302808 A | 11/1995 |
| JP | 09-107327 | 4/1997 |
| JP | 97/26634 A1 | 7/1997 |
| JP | 2000-505216 A | 4/2000 |
| JP | 2000-299066 A | 10/2000 |
| JP | 2002-042273 A | 2/2002 |
| JP | 2002-111838 A | 4/2002 |
| JP | 2002-329552 A | 11/2002 |
| JP | 2003-115949 A | 4/2003 |
| JP | 2003-524362 A | 8/2003 |
| JP | 2004-235724 A | 8/2004 |
| JP | 2004-297629 A | 10/2004 |
| JP | 2005-079225 A | 3/2005 |
| JP | 2005-172083 A | 6/2005 |
| JP | 2006-277129 A | 10/2006 |
| JP | 2007-279616 A | 10/2007 |
| JP | 2008-018476 A | 1/2008 |
| JP | 2009-505386 A | 2/2009 |
| JP | 04274598 B2 | 6/2009 |
| JP | 2009-178805 A | 8/2009 |
| JP | 2009-529276 A | 8/2009 |
| JP | 2009-259937 A | 11/2009 |
| JP | 2009-292135 A | 12/2009 |
| JP | 2010-011205 A | 1/2010 |
| JP | 2010-035036 A | 2/2010 |
| JP | 2010-225715 A | 10/2010 |
| JP | 2011-171894 A | 9/2011 |
| JP | 2012-500487 A | 1/2012 |
| JP | 2012-074798 A | 4/2012 |
| JP | 2016176913 A * | 10/2016 |
| KR | 20100006616 U | 6/2010 |
| WO | 03/065691 A2 | 8/2003 |
| WO | 2006/028030 A1 | 3/2006 |
| WO | 2010/020753 A2 | 2/2010 |
| WO | 2011/037921 A1 | 3/2011 |
| WO | 2011/064737 A2 | 6/2011 |
| WO | 2012/108443 A1 | 8/2012 |
| WO | 2014/110106 A1 | 7/2014 |

OTHER PUBLICATIONS

MobilePhoneHospital.conn, Mobile Phone Repairing Notes, Solutions, Diagrams: Introduction about Mobile Phone IC's (Integrated Circuits). www.mobilephonehospital.com, Nov. 2011 (Year: 2011).*

(56) References Cited

OTHER PUBLICATIONS

Bott et al., "Windows 7, Official Manual," vol. 2, Nikkei BP, Apr. 24, 2010, First Edition, pp. 315-316, book.

Matthew Braga, "Stay dry: Where to find your phone's water sensors," tested.com, Aug. 16, 2010, website available at: http://www.tested.com/tech/smartphones/720-stay-dry-where-to-find-your-phones-water-sensors/.

Neil Hughes, "Apple looking to improve water sensors for detecting iPhone damage," appleinsider.com, Feb. 17, 2012, website available at: http://appleinsidercom/articles/12/02/17/apple_looking_to_improve_water_sensors_for_detecting_iphone_damage.

Kevin Purcell, "How to find your mobile phone's water sensor," notebooks.com, Aug. 16, 2010, website available at: http://notebooks.com/2010/08/16/how-to-find-your-mobile-phones-water-sensor/.

United States Patent and Trademark Office acting as the International Searching Authority, "International Search Report and Written Opinion," dated Jan. 29, 2015, in international patent application No. PCT/US2014/050732.

* cited by examiner

METHODS, APPARATUSES AND SYSTEMS FOR SENSING EXPOSURE OF ELECTRONIC DEVICES TO MOISTURE

CROSS REFERENCE TO RELATED APPLICATIONS

This application is a continuation-in-part of U.S. patent application Ser. No. 13/734,779 filed on Jan. 4, 2013, titled METHODS, APPARATUSES AND SYSTEMS FOR MONITORING FOR EXPOSURE OF ELECTRONIC DEVICES TO MOISTURE AND REACTING TO EXPOSURE OF ELECTRONIC DEVICES TO MOISTURE ("the '779 application"). The '779 application includes a claim for the benefit of priority under 35 U.S.C. § 119(e) to the Jan. 10, 2012, filing date of U.S. Provisional Patent Application No. 61/584,933, titled METHODS, APPARATUS AND SYSTEMS FOR MONITORING AND REACTING TO EXPOSURE OF ELECTRONIC DEVICES TO MOISTURE ("the '933 Provisional Application").

This application is also a continuation-in-part of U.S. patent application Ser. No. 14/320,799 filed on Jul. 1, 2014, titled APPARATUSES, SYSTEMS, AND METHODS FOR DETECTING AND REACTING TO EXPOSURE OF AN ELECTRONIC DEVICE TO MOISTURE ("the '799 application"). The '799 application is a continuation of U.S. patent application Ser. No. 14/150,534 filed on Jan. 8, 2014, titled APPARATUSES, SYSTEMS, AND METHODS FOR DETECTING AND REACTING TO EXPOSURE OF AN ELECTRONIC DEVICE TO MOISTURE, now U.S. Pat. No. 8,773,271, issued on Jul. 8, 2014 ("the '534 application"). The '534 application claimed the benefit of priority under 35 U.S.C. § 119(e) to the Jan. 8, 2013, filing date of U.S. Provisional Patent Application No. 61/750,328, titled APPARATUSES, SYSTEMS, AND METHODS FOR DETECTING AND REACTING TO EXPOSURE OF AN ELECTRONIC DEVICE TO MOISTURE ("the '328 Provisional Application"). The entire disclosures of the '779 Application, the '933 Provisional Application, the '799 Application, the '534 application and the '328 Provisional Application are, by this reference, incorporated herein.

TECHNICAL FIELD

This disclosure relates generally to methods, devices, and systems for sensing exposure of electronic devices to moisture and for responding to exposure of electronic devices to moisture, and to electronic devices that employ such a method and/or system.

SUMMARY

In one aspect, the present disclosure relates to a system for sensing exposure of an electronic device to moisture (e.g., liquid, vapor, etc.) (e.g., as moisture enters the electronic device through an entry point, such as a port, seam or crack). In addition to sensing moisture, the system may be configured to alter or vary operation of the electronic device. Similarly, in a method for sensing exposure of an electronic device to moisture, the manner in which the electronic device operates may be varied or altered if a predetermined amount of moisture is detected. Various aspects relating to systems and methods for sensing exposure of electronic devices to moisture are disclosed.

The term "moisture" is used throughout this disclosure to refer to a variety of liquids and vapors. Without limitation, moisture may include water, aqueous solutions (e.g., salt solutions, acidic solutions, basic solutions, drinks, etc.) or vapors of water or other aqueous materials (e.g., humidity, fogs, mists, etc.). Moisture may also include organic liquids and vapors (e.g., organic solvents, low molecular weight organic compounds, etc.), including electrically conductive organic materials, as well as a variety of other substances or conditions that might pose a threat to an electronic device or its components.

A moisture sensing system may be used in conjunction with or incorporated into a variety of different types of electronic devices, including, without limitation, portable electronic devices, such as mobile telephones, smart phones, e-readers, tablet computers, laptop computers, and the like; electronic devices that are expected to be used in environments where exposure to moisture is possible or even likely, such as electronic devices used in agricultural equipment, irrigation, public safety, military, the oil and gas industry, transportation (e.g., by railways, in trucking, etc.), maritime applications; and electronic devices that are used in a variety of other applications.

In some embodiments, a moisture sensing system may include a moisture sensor, a control element, a heating element, a warning element, a switch, or any combination thereof. The control element, the heating element, the warning element, the switch, a power supply for these features, and electrical connections and other components of a moisture sense system may be made moisture resistant (e.g., covered with a moisture-resistant coating, etc.). The moisture sensor may also be moisture resistant (e.g., portions of the moisture sensor may be sealed, covered with a moisture-resistant coating, etc.).

The moisture sensor enables sensing moisture in an environment where the moisture sensor, and any electronic device with which it is associated (or is a part), is located. The moisture sensor may be located within an electronic device, exposed to the interior of the electronic device, exposed to an exterior of the electronic device, or some combination thereof. The moisture sensor may comprise a capacitance sensor configured to measure the dielectric properties of the ambient conditions to which an electronic device is exposed (i.e., to sense moisture), an inductive sensor for measuring magnetic properties of an electronic device (i.e., to sense moisture), or both. In one specific embodiment, the moisture sensor includes one or more capacitance sensors, each of which being incorporated into an integrated circuit. In another embodiment, the moisture sensor includes one or more capacitance sensors, each having a sensor element and a shield coupled to an input port of an integrated circuit. A capacitance sensor may be configured for detecting a change in a dielectric constant between two parallel electrodes. In yet another embodiment, the moisture sensor includes an inductive sensor including a coil coupled to an integrated circuit and configured for generating a magnetic field and detecting a change in magnetic permeability. In yet another embodiment, the moisture sensor may comprise an inductive component and/or a capacitive component, which may also be used for one or more other functions in addition to sensing moisture. More specifically, as one example, one or more antennas of an electronic device may be used to sense moisture (e.g., via capacitive and/or inductive sensing methods).

The control element may control operation of other components of the moisture sense system. The control element may be dedicated to the moisture sense system, or it may comprise a processing element of the electronic device with which the moisture sense system is used.

The warning element, which may operate under control of the control element, may be configured to generate one or more signals indicative of exposure of the electronic device to moisture. In some embodiments, the warning element may be configured to notify an individual using the electronic device that the electronic device has been exposed to an above-ambient amount of moisture, that the amount of moisture to which the electronic device has been exposed exceeds per-exposure threshold of moisture, that the cumulative amount of moisture to which the electronic device has been exposed over a period of time (e.g., the life of the electronic device, the past year, the past six months, the past month, etc.) has exceeded a total acceptable exposure amount, the amount of moisture to which the electronic device has been exposed (e.g., the type of moisture to which the electronic device is currently exposed, the amount of moisture to which the electronic device is currently exposed, the amount of time the electronic device was/is exposed to moisture during a particular moisture-exposure event, the total amount of time the electronic device has been exposed to moisture over a period of time (e.g., the life of the electronic device, the past year, the past six months, the past month, etc.), the number of times the electronic device has been exposed to moisture, etc.), other information about exposure of the electronic device to moisture, or any combination of the foregoing. Any of the moisture thresholds mentioned above may be referred to herein as a "moisture event threshold." In embodiments where the electronic device is configured for wireless communication (e.g., a mobile telephone, a smart phone, a tablet computing device, a portable digital music player, a radio, a wireless automobile entry device (i.e., key), etc.), the warning element may be configured to notify a remote monitoring service that the electronic device has been exposed to an amount of moisture that meets or exceeds a moisture event threshold.

The switch, which may operate under control of the moisture sensor or the control element, may be configured to move between a normal position and a moisture event position. With the switch in the normal position, the electronic device may operate normally; the switch allows power to flow from a power supply of the electronic device to its primary electronic components (e.g., electronic components that enable the electronic device to function as intended, etc.). In the moisture event position, the switch may terminate the communication of power from a power supply to at least some of the circuitry of the electronic device (e.g., electronic components that enable the electronic device to function as intended, etc.). In some embodiments, when the switch is in the moisture event position, it may allow power to be communicated from the power supply to a remainder of the moisture sense system.

In some embodiments, a change in the orientation of the switch may cause a mechanical action in the electronic device that may temporarily seal one or more of its moisture-sensitive components from exposure to the moisture that has been detected.

In another aspect, methods for responding to exposure of an electronic device to amounts of moisture that meet or exceed the moisture event threshold include monitoring an amount of moisture to which the electronic device is exposed. Monitoring may occur continuously or periodically. If the amount of moisture exceeds a predetermined moisture event threshold, a normal operational mode of the electronic device may be terminated, and a moisture event mode of the electronic device may be initiated.

As an electronic device exits its normal operational mode, the supply of power from a power supply (e.g., a battery, a supercapacitor, a fuel cell, a photovoltaic cell, etc.) to one or more components of the electronic device may be terminated. Termination of the supply of power to these components may protect them from damage (e.g., damage from short circuits or accelerated corrosion that may be caused by water, other types of moisture, etc.). In some embodiments, this moisture event mode of the electronic device may include a complete shut-down of the electronic device. In other embodiments, the moisture event mode of the electronic device may comprise a safe mode, in which certain components of the electronic device (e.g., components that have been made moisture-resistant, components that are unlikely to fail when exposed to moisture, etc.) may continue to operate. In some embodiments, operation of the electronic device in the safe mode may enable a moisture sense system to continue operation, while all other components of the electronic device (i.e., those that do not participate in the moisture sense system) may shut down.

As an electronic device enters the safe mode, or moisture event mode, the electronic device or a moisture sense system associated with the electronic device may generate a notification. Without limitation, the notification may include a user-perceptible warning, the generation and transmittal of a signal to a remote monitoring service (e.g., by way of an e-mail, an SMS text message, an MMS text message, etc.), or a combination of these services.

In embodiments where moisture monitoring continues while an electronic device is in moisture event mode, once the amount of moisture to which the electronic device is exposed drops to an acceptable level, the electronic device may be enabled to resume full operation. In such an embodiment, when the amount of moisture detected drops to or below a predetermined reset threshold, which may be the same as or different from the moisture event threshold, the moisture event mode of the electronic device may be terminated, and the normal operational mode of the electronic device may be reinitiated.

Programs or applications (or "apps") that are launched or executed in response to detection of amounts of moisture that meet or exceed a moisture event threshold are also disclosed. Such a program or application may perform functions that relate to exposure of an electronic device to moisture. By way of non-limiting example, a program or application that is executed or launched upon exposure of an electronic device may provide a user with information about exposure of the electronic device to moisture. Such information may include, but is not limited to, information on the amount of moisture to which an electronic device has been exposed, information on prior exposure of the electronic device to moisture, cumulative moisture exposure information, diagnostic and/or historic information. As another non-limiting example, a program or application that launches, or executes, upon exposure of an electronic device to an amount of moisture that meets or exceeds a predetermined moisture event threshold may provide a user with information on moisture-resistant elements of the electronic device (e.g., the last time a moisture-resistant coating was applied to components of the electronic device, etc.).

Other aspects, as well as features and advantages of various aspects, of the disclosed subject matter will become apparent to those of ordinary skill in the art though consideration of the ensuing description, the accompanying drawings and the appended claims.

DETAILED DESCRIPTION

Figure 1:
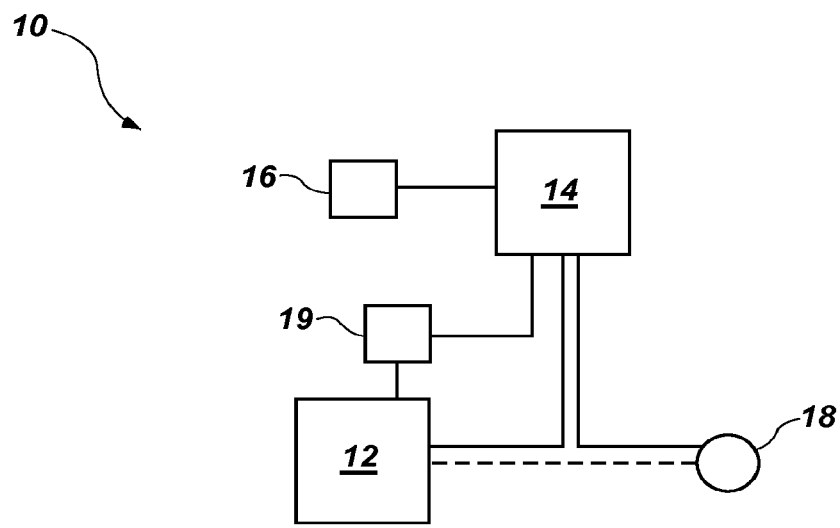
FIG. 1 is a schematic representation of a moisture sense system.

With reference to FIG. 1, an embodiment of a system 10 is illustrated. System 10 may also be referred to herein as a "moisture sense system." The moisture sense system 10, which is configured for use with an electronic device (e.g., a portable electronic device, an electronic device that is expected to be used in an environment where exposure to moisture is likely or even expected, etc.), may be configured to sense if the electronic device is exposed to moisture. In the embodiment illustrated by FIG. 1, the moisture sense system 10 includes a moisture sensor 12, a control element 14, a warning element 16, and a switch 18. As will be described more fully below, system 10 may also include a heating element 19 for generating heat in response to sensing moisture (i.e., a moisture event) within the electronic device. In some embodiments, the moisture sense system 10 may include a dedicated power source (e.g., a capacitor, a supercapacitor, a battery, etc.).

The moisture sensor 12 enables sensing moisture and monitoring of an amount of moisture in an environment where it is located. The moisture sensor 12 may be configured for assembly with an electronic device. The moisture sensor 12 (and other components of the moisture sense system 10) may be configured to operate regardless of whether the electronic device is powered on (e.g., in embodiments where the moisture sense system 10 receives power from a backup power supply of the electronic device, a dedicated power source, etc.). Various embodiments of moisture sensors 12 may be used in a moisture sense system 10 that incorporates teachings of this disclosure. As non-limiting examples, moisture sensor 12 may comprise one or more capacitance sensors, one or more inductive sensors, or any combination thereof.

The moisture sensor 12 may communicate with the control element 14, which may be configured to process signals from the moisture sensor 12 and, upon detecting signals indicative of certain conditions (e.g., an amount of moisture that meets or exceeds a predetermined moisture event threshold, an amount of moisture at or below a predetermined reset threshold, etc.), execute commands that control operation of other components of the moisture sense system 10. The control element 14 may comprise a dedicated processing element (e.g., a microcontroller with embedded firmware, etc.) or it may comprise a processor of an electronic device with which the moisture sense system 10 is associated. Further, control element 14 may include logic, such as logic 212 shown in FIG. 4.

One of the components of the moisture sense system 10 that may operate under control of the control element 14 is the warning element 16. The warning element 16 may be configured to alert a user of the electronic device of its exposure to moisture. In such an embodiment, the warning element 16 may comprise a visible alarm, an audible alarm, a vibrating alarm, or the like. In some embodiments, the warning element 16 may comprise a display or monitor (e.g., the display or monitor of an electronic device with which the moisture sense system 10 is associated, or of which the moisture sense system 10 is a part, etc.), which may display a warning. In embodiments where the warning element 16 comprises a display or monitor, it may provide a user interface (e.g., display images, receive inputs (when the display or monitor is touch-sensitive), etc.) with the control element 14 while the control element 14 executes a program, or application or "app," in response to detection by the moisture sensor 12 of an amount of moisture that meets or exceeds a moisture event threshold. In embodiments where the control element 14 launches a program or application in response to detection of an amount of moisture that meets or exceeds the moisture event threshold, the warning element 16 may display information that relates to exposure of an electronic device to moisture. By way of non-limiting example, a program or application that is executed or launched upon exposure of an electronic device may provide a user with information about exposure of the electronic device to moisture. Such information may include, but is not limited to, information on the amount of moisture to which an electronic device has been exposed, depth of moisture exposure, information on prior exposure of the electronic device to moisture, cumulative moisture exposure information, diagnostic information, historical information, other information that relates to exposure of the electronic device to moisture, or combinations of any of the foregoing. The information provided to the user may also be stored locally on the electronic device, and remain available for subsequent access by a user of that electronic device. As another example, a program or application that launches upon exposure of an electronic device to moisture in an amount that meets or exceeds a moisture event threshold may provide a user with information on one or more moisture-resistant features of the electronic device (e.g., the last time a moisture-resistant coating was applied to components of the electronic device, etc.). In another example, the control element 14 may execute a program or an application that provides a user with instructions on how to minimize moisture-related damage to the electronic device with which the moisture sense system 10 is associated; e.g., instructions on a protocol for removing moisture from, or drying, the specific electronic device with which the moisture sense system 10 is associated. Other examples of information that the control element 14 may cause the warning element 16 to provide to a user include, but are not limited to, warranty information, repair information, advertisements relating to mitigating the effects of potential damage from exposure of the electronic device to moisture, and other moisture-related information.

The warning element 16 may comprise a wireless communication element, and may be configured to transmit a signal to a remote monitoring service. A wireless communication element may comprise a primary communication element of the electronic device with which the moisture sense system 10 is associated, or it may comprise a dedicated wireless communication system. In either embodiment, under control of the control element 14, the warning element 16 may identify an appropriate recipient for information regarding exposure of the electronic device to an above-ambient amount of moisture, and transmit that information to its intended recipient. A wireless communication element may be configured to communicate by a radiofrequency (RF) communication scheme, such as GSM, TDMA (time division multiple access), CDMA (code division multiple access), LTE (long term evaluation), 3G, 4G, NFC (near field communications) or the like. Alternatively, a wireless communication element may be configured to communicate by optical means, such as an infrared (IR) signal, an optical local area network (LAN) system, an optical personal area network (PAN) system, or the like. Examples of wireless communication elements include, without limitation, radiofrequency (RF) communication components, such as cellular transmitters, Bluetooth transmitters or the like, WiFi transmitters (i.e., systems operating on IEEE 802.xxx protocols), or the like.

The switch 18 may also operate in accordance with signals from the control element 14. Alternatively, the switch 18 may be controlled directly by signals from the moisture sensor 12. In either event, the switch 18 may limit the communication of power from a power supply 816 (see FIG. 9) (e.g., a primary battery, a rechargeable battery, a back-up battery, a dedicated battery, a supercapacitor, a fuel cell, a photovoltaic cell, etc.) to moisture-sensitive components (e.g., electronic components, etc.) of the electronic device with which the moisture sense system 10 is associated, or of which the moisture sense system 10 is a part. In some embodiments, the control element 14 may be configured (e.g., programmed, etc.) to determine the orientation of the switch 18 and, thus, the portions of the electronic device and/or the moisture sense system 10 to which power is to be terminated.

The switch 18 may have a normal position, or orientation, and at least one moisture event position, or orientation. When the switch 18 is in the normal position, the electronic device may operate normally; the switch allows power to flow from a power supply of the electronic device to its primary electronic components (e.g., electronic components that enable the electronic device to function as intended, etc.). When in a moisture event position, the switch 18 may terminate the communication of power from the power supply 816 to at least some of the circuitry of the electronic device (e.g., electronic components that enable the electronic device to function as intended, one or more communication ports, displays, sensors, cameras, speakers, microphones, etc.). In some embodiments, when the switch 18 is in a moisture event position, it may allow power to be communicated from the power supply 20 to a remainder of the moisture sense system 10. If operation of the primary power supply of the electronic device is adversely effected by the moisture, power may be communicated to the remainder of the moisture sense system 10 by way of a backup battery, a capacitor, supercapacitor or battery dedicated to the moisture sense system 10, etc.

One or more of the control element 14, the warning element 16, the switch 18, the power supply 816, heating element 19, and electrical connections and other components of a moisture sense system 10 may be rendered resistant to one or more types of moisture (e.g., to water, aqueous solutions, water vapor, vapors of aqueous solutions, organic liquids or vapors, etc.). For example, one or more of these components may be covered with a moisture-resistant coating, such as a coating that is impermeable or substantially impermeable to moisture (e.g., a substituted or unsubstituted polyp-xylylene) polymer (i.e., a parylene, etc.), etc.) a moisture-repellant coating, etc. The moisture sensor 12 may also be moisture resistant (e.g., all or a portion of the moisture sensor may be covered with a moisture-resistant coating, etc.).

According to various embodiments, the moisture sense system 10 may be calibrated based one or more parameters.

More specifically, one or more threshold level settings, which may define a moisture event, may be recalibrated based on one or more parameters. For example, the moisture sense system 10 may be calibrated based on environmental conditions, such as humidity, temperature, etc, at a location of the moisture sense system 10. As a more specific example, the moisture sense system 10 may be configured to recalibrate upon experiencing a change in an environment, such as a being relocated from a dry environment (e.g., a desert) to a relatively humid environment. It is noted that calibration of moisture sense system 10 may include user initiated calibration, user verified calibration, automatic calibration, manual calibration, etc. Further, the moisture sense system 10 may utilize hysteresis to prevent unwanted rapid switching between a moisture event "ON" level and a moisture event "OFF" level. Stated another way, once a moisture event is detected at a first moisture level, the moisture level sensed by the moisture sense system 10 must fall below the first moisture level before the moisture event is abated.

As will be appreciated by a person having ordinary skill in the art, moisture (e.g., water) may have dielectric properties that are different (i.e., stronger) than air. As will be further appreciated, a capacitance sensor may be configured for measuring dielectric strength and, thus, a capacitance sensor may be used to sense moisture. As a non-limiting example, a capacitance sensor may include two parallel electrodes (e.g., two parallel plates), wherein a voltage at a one electrode may be sensed in response to conveying an AC voltage to the other electrode. A value of the sensed voltage may be used to determine which one or materials may be present between the two parallel electrodes. For example, a value of a voltage sensed when only air is present between the parallel electrodes will differ than a value of the sensed voltage when air and liquid are present between the parallel electrodes.

In accordance with one embodiment of the present disclosure, the moisture sensor 12 may comprise a capacitance sensor, which may be configured to generate an output that may be indicative of moisture proximate thereto. Further, it is noted that the output of the capacitance sensor may vary depending on an amount of moisture proximate thereto. According to one specific example, moisture sensor 12 may include at least one capacitance sensor, which may be part of or coupled to an integrated circuit (IC). More specifically, in one embodiment, a capacitance sensor may be internal to an IC, such that the IC may be configured to measure a dielectric proximate (e.g., directly above) thereto.

In another embodiment, moisture sensor 12 may include at least one capacitance sensor, which is at least partially external to the IC and coupled to one or more input ports of the IC. In this embodiment, moisture sensor 12 may include a shield at least partially surrounding a sensor element and including a gap between the sensor element and the shield where moisture is to be detected.

According to one embodiment, the IC may be coupled to and configured to drive a heating element (e.g., heating element 19) upon sensing moisture. The heating element may be configured for generating heat, which may assist in drying at least portion of an electronic device (i.e., to prevent moisture from lingering).

Figure 2:
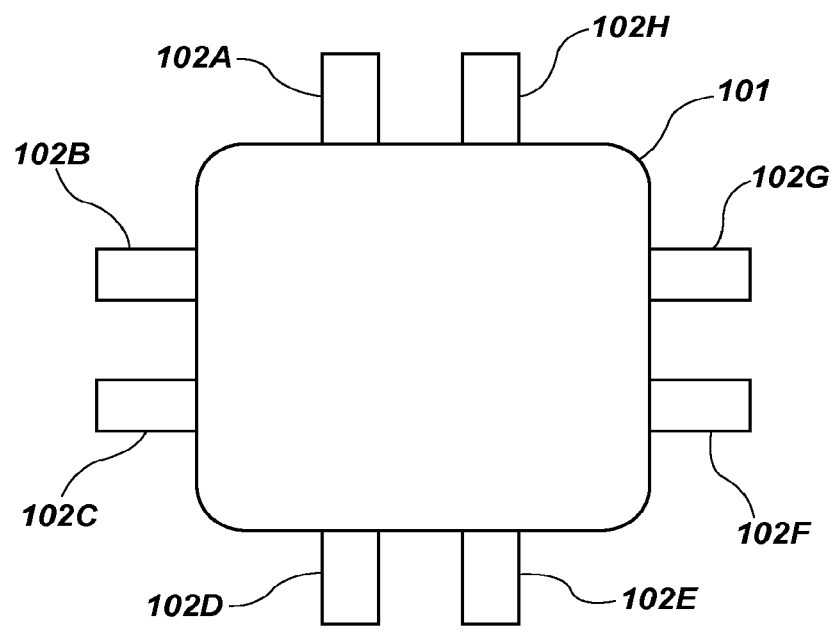
FIG. 2 depicts an embodiment of an integrated circuit including a plurality of ports.

FIG. 2 illustrates an embodiment of an IC 101 including a plurality of ports 102. According to one embodiment, ports 102 may include a plurality of input ports 102A-102G, and at least one output port 102H. Although IC 101 is illustrated as having eight ports, IC may have any number of input ports and any number of output ports. As described more fully below, IC 101 may include or may be coupled to a sensor for sensing moisture proximate thereto.

Figure 3:
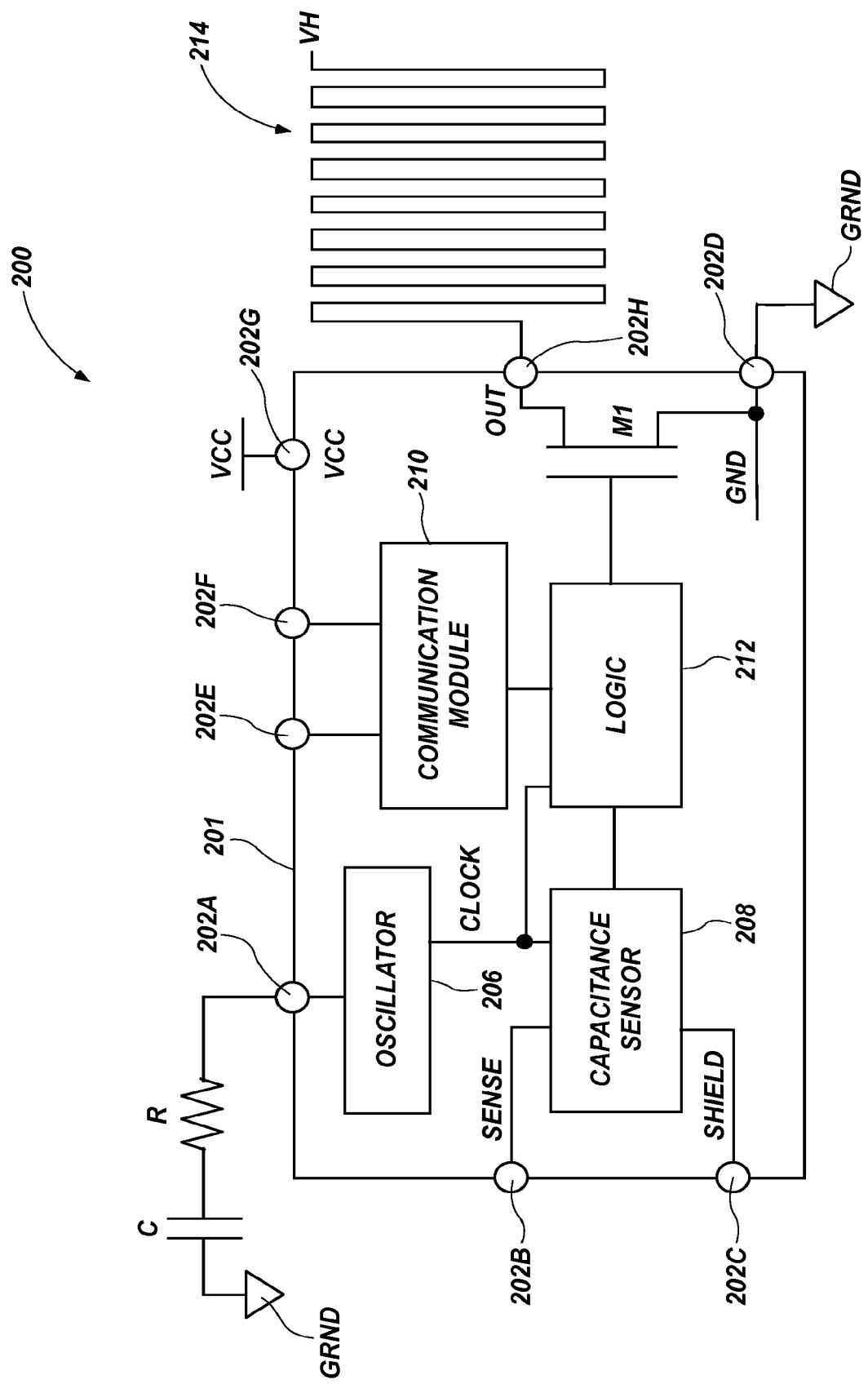
FIG. 3 is a block diagram illustrating an embodiment of an integrated circuit coupled to a heating element.

FIG. 3 is a block diagram depicting an embodiment of a moisture sense system 200 including an IC 201 having a plurality of inputs ports 202A-202G and an output port 202H. Further, IC 201 may include an oscillator 206 having an input coupled to port 202A, which is further coupled to ground voltage GRND via a resistor R and a capacitor C. As an example, oscillator 206 may comprise a low-power RC oscillator configured to convey a sine wave. IC 201 also includes a capacitance sensor 208 having a one input coupled to port 202B and another input coupled to port 202C. As will be described more fully below, port 202B may be coupled to a sensor element and port 202C may be coupled to a shield. As will be understood by a person having ordinary skill in the art, capacitance sensor 208, which may include an AC measurement circuit, may be configured to measure a dielectric constant between two electrodes based on a RC time constant decay rate. Capacitance sensor 208 may be configured to convey an output signal, which is indicative of the dielectric constant between two electrodes (e.g., the sensor element and the shield).

IC 201 may further include a communication module 210 having one input coupled to port 202E and another input coupled to port 202F. Moreover, IC 201 may include logic 212 configured for receiving a signal from the capacitor sensor 208, a clock signal from oscillator 206, and a signal from communication module 210. In addition, IC 201 may include a transistor M1 having a gate coupled to an output of logic 212, a source coupled to a ground voltage GRND via port 202D, and a drain coupled to output port 202H, which is further coupled to a supply voltage VCC via port 202G.

Moisture sense system 200 may also include a heating element 214, which may comprise any known and suitable heating element. According to one embodiment, heating element 214 may comprise one or more heating traces, as illustrated in FIG. 3. As noted above, in response to a moisture event, heating element 214 may be configured for generating heat, which may help dry at least portion of an electronic device (i.e., to prevent moisture from lingering). As will be appreciated by a person having ordinary skill in the art, corrosion of a device part may be a function of an amount of time the device part is exposed to moisture. Thus, it may be advantageous to quickly dry critical, non-protected parts (e.g., speakers, connectors with exposed contacts and other semi-protected components that have to be masked during a water-proofing process) of an electronic device to prevent long-term damage.

Logic 212 may be configured for determining when a moisture event occurs and when a moisture event abates. More specifically, based on a signal received from capacitance sensor 208, logic 212, which may be calibrated based on one or more conditions, may determine whether or not moisture is proximate capacitance sensor. Upon determining that a moisture event is occurring, logic 212 may generate a control signal, which may cause transistor M1 to conduct. It is noted that logic 212 may be externally programmable through the communications module 210 via, for example, an inter-integrated circuit (I2C) bus or a serial peripheral interface (SPI) bus. It is noted that communication module 210 may also be configured to turn on/off the heating element 214 remotely when a moisture event is not occurring. The IC 201 may further include one or more outputs programmable to disable circuitry (e.g., upon detection of a moisture event).

Figure 4:
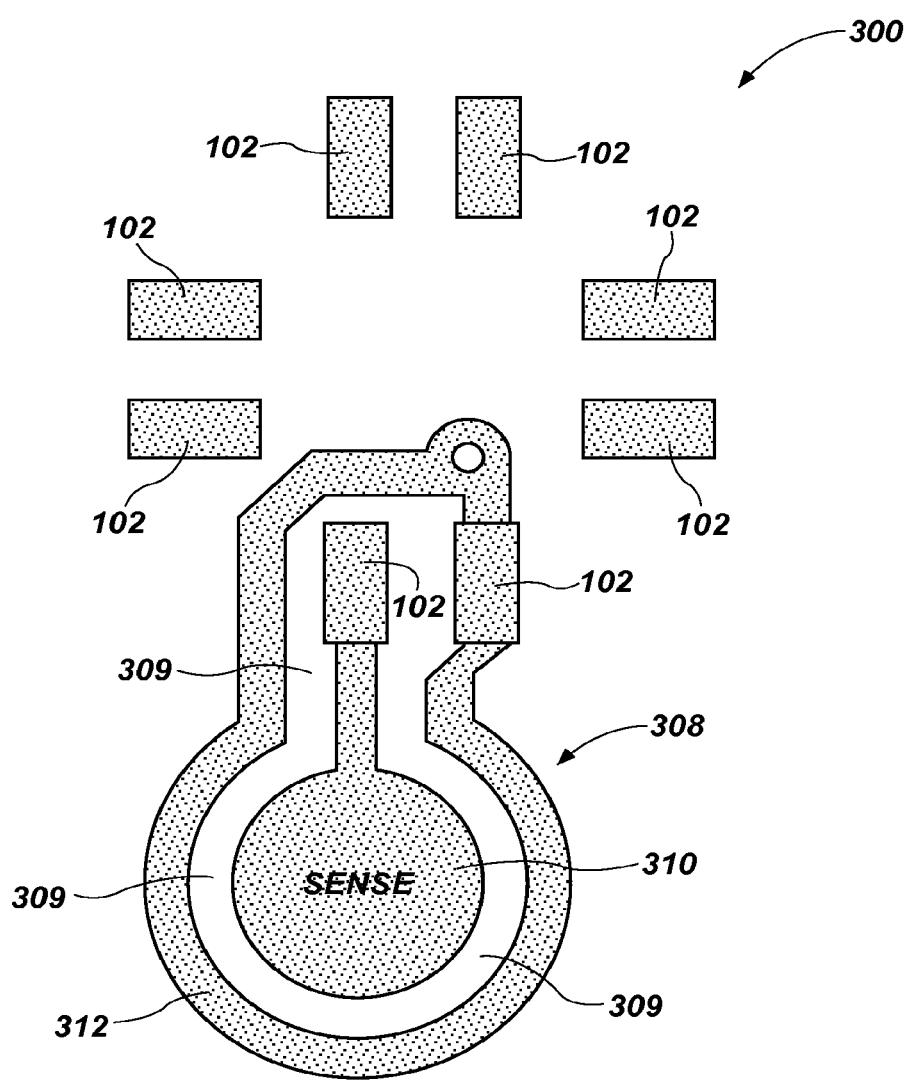
FIG. 4 illustrates a system including an integrated circuit and a moisture sensor.

FIG. 4 is an illustration of an embodiment of a moisture sense system 300 including a capacitance sensor 308 coupled to a plurality of input ports 102 of an IC (e.g., IC 101 illustrated in FIG. 2). Capacitance sensor 308 includes a sensor element 310 and a shield 312, which at least partially surrounds sensor element 310. Further, an air gap 309 may exist between sensor element 310 and shield 312 where moisture may be detected. The capacitance sensor 308, which may be configured to receive an AC voltage, is at least partially surrounded by the shield 312, which may be coupled to a ground voltage. The shield 312 surrounds the sensor element 310 except where moisture detection is desired. It is noted that by increasing the size of sensor element 310 and shield 312 (i.e., increasing the surface area), the sensitivity of capacitance sensor 308 may be increased.

According to one embodiment, an electronic device may include one or more sensor elements and shields positioned within the electronic device and coupled to one or more ICs. Further, it is noted that although FIG. 4 illustrates a capacitance sensor at least partially external (i.e., remote from) an IC, the present invention is not so limited. Rather, a capacitance sensor, including a sensor element and an shield, may be internal to an IC. It is further noted that the moisture sense system 300 may include components similar to the components illustrated in the moisture sense system 200 of FIG. 2 More specifically, for example, moisture sense system 300 may include a communication module, logic, oscillator, and/or a heating element.

Figure 5:
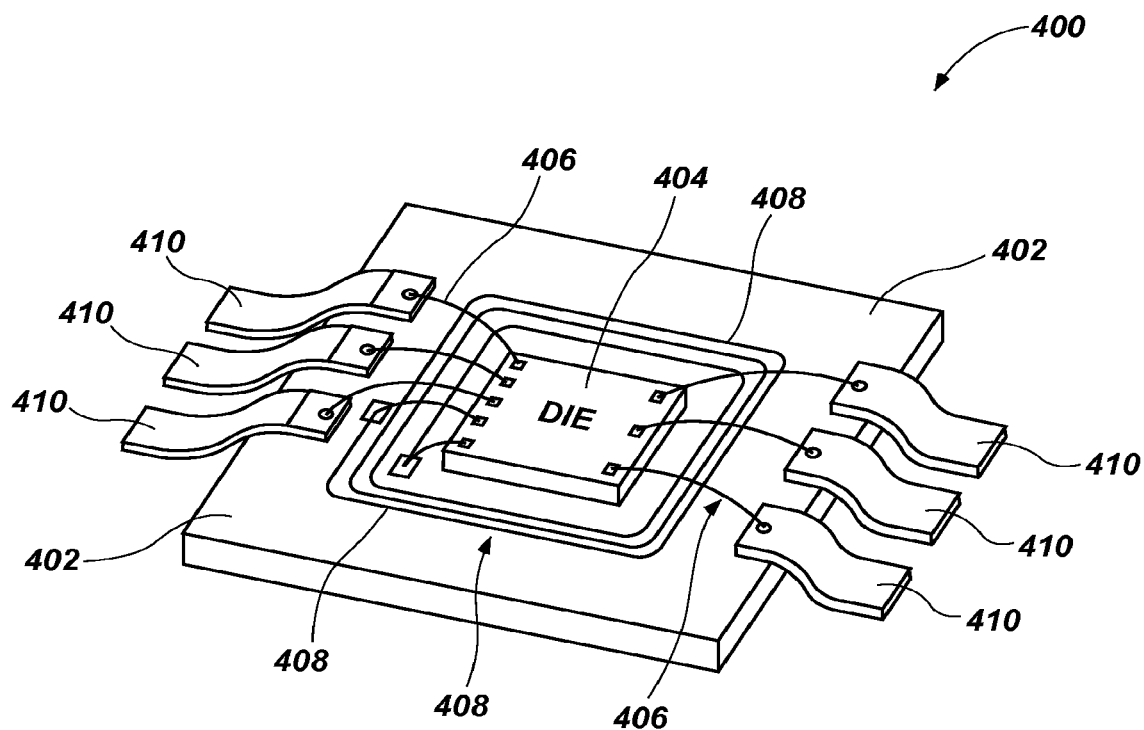
FIG. 5 depicts an embodiment of a system including an integrated circuit and an inductive coil.

Whereas a capacitance sensor can detect moisture by measuring dielectric strength, an inductive sensor may detect moisture by measuring a change in magnetic permeability (i.e., air vs liquid). As will be appreciated, when a current is induced into a coil, the coil may generate a magnetic field. The formation and decay of the magnetic field may be slowed by the presence of highly permeable materials. In accordance with another embodiment of the present disclosure, moisture sensor 12 (see FIG. 1) may comprise an inductive sensor. FIG. 5 depicts an embodiment of a system 400 including a substrate 402, an IC 404 positioned on the substrate 402, a plurality of wire bonds 406 (i.e., for coupling the IC 404 to conductive traces 410), and an inductive coil 408. It is noted that the ends of inductive coil 408 may be wire-bonded to IC 404. According to one embodiment, the inductive coil 408 may be configured to generate a magnetic field, which may extend beyond the boundaries of substrate 402. During a contemplated operation, IC 404 may pulse the inductive coil 408 (i.e., with a voltage pulse) and measure an electrical current response, which may vary depending on how fast the magnetic field can build and decay. A decay rate of the magnetic field may depend on a presence of one or more materials, such as liquid and/or air (i.e., liquid v. air dielectric may change the magnetic field response). According to one embodiment, IC 404 may include a calibration pin, which may be used to determine an ambient response for calibrating system 400. As will be appreciated, a temperature of system 400 may affect the decay rate of the magnetic field and, therefore, system 400 may include a temperature sensor (not shown in FIG. 5) for sensing a temperature, which may be used by a control element in determining whether a moisture event has occurred.

Figure 6:
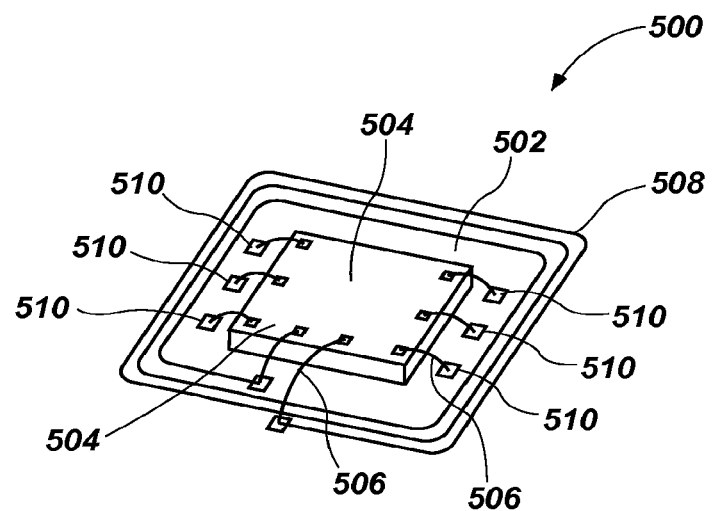
FIG. 6 depicts another embodiment of a system including an integrated circuit and an inductive coil.

FIG. 6 illustrates another embodiment of a system 500 including a substrate 502, an IC 504 positioned on the substrate 502, a plurality of wire bonds 506 coupled to the IC 504, and an inductive coil 508. It is noted that the ends of the inductive coil 508 may be wire-bonded to the IC 504.

Further, in this embodiment, the inductive coil 2508 may at least partially surround wire bonds 506 and conductive traces 510.

Figure 7:
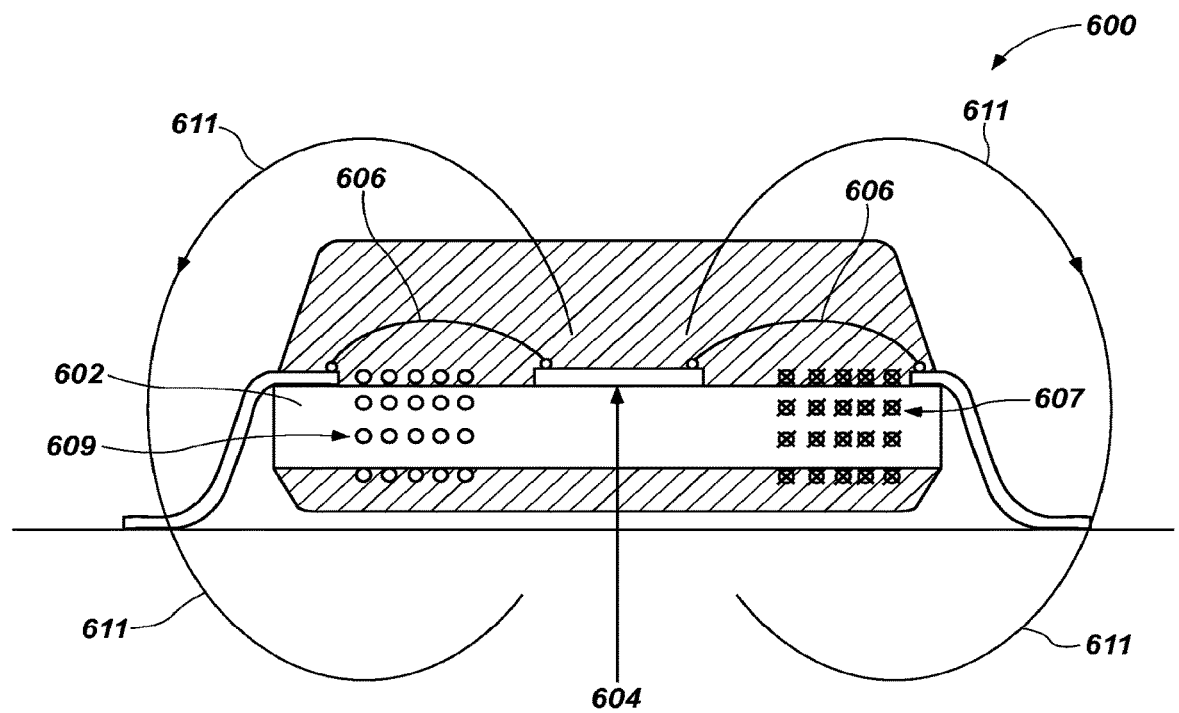
FIG. 7 is a cross-sectional illustration of a system including an integrated circuit positioned on a substrate.

FIG. 7 is a cross-sectional illustration of a system 600 including a substrate 602, an IC 604 positioned on the substrate 602, and a plurality of wire bonds 606 coupled to the IC 604. Further, FIG. 7 depicts a magnetic field, which is depicted by reference numeral 611 and may be generated by an inductive coil (e.g., coil 260 or coil 280). It is noted that the inductive coil is depicted as conductors with current running into the page (illustrated by "O" 609) and conductors with current running out of the page (illustrated by "X" 607).

Figure 8:
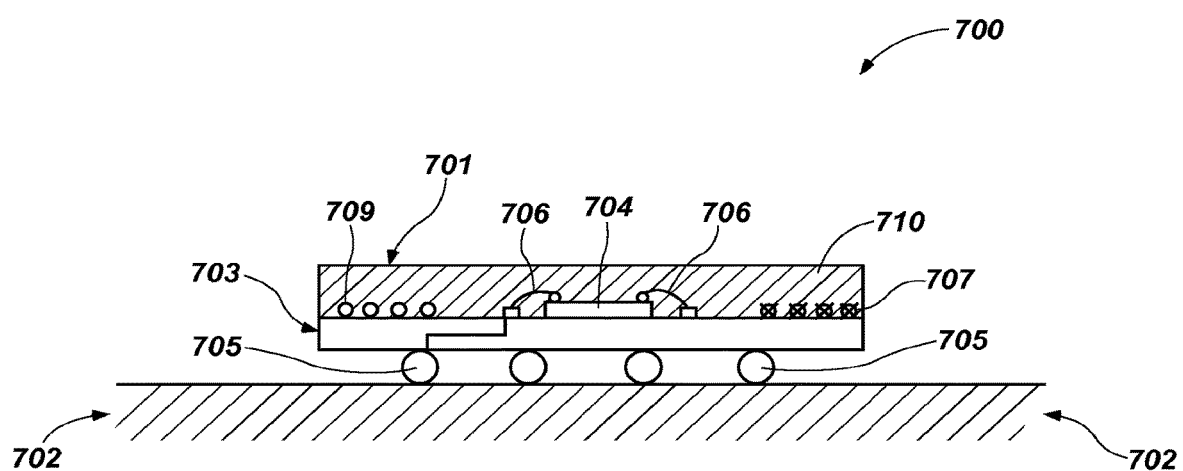
FIG. 8 is a cross-sectional illustration of a package including an integrated circuit.

FIG. 8 is a cross-sectional view of a system 700 including an example package 701 according to one embodiment of the present disclosure. According to one embodiment, package 701 may comprise a ball grid array (BGA) package. As will be understood by a person having ordinary skill in the art, a BGA may be advantageous because a BGA substrate may comprise a printed circuit board for routing signals, a detection coil can be made larger (i.e., for better sensitivity), and the detection coil may be a simple etched feature of a printed circuit board. Package 701 includes a BGA substrate 703 coupled to a printed circuit board 702 via one or more solder balls 705. Further, package 701 may include an IC 704, wire bonds 706, and an encapsulation 710 (e.g., an epoxy encapsulation). It is noted that an inductive coil is depicted as conductors with current running into the page (illustrated by "O" 709) and conductors with current running out of the page (illustrated by "X" 707).

It is noted that although the embodiments illustrated in FIGS. 5-8 are directed to an on-chip inductive coil the present invention is not so limited. Rather, embodiment of the present disclosure may include remote (off chip) sensing accomplished by pulsing an external loop sensor or air dielectric inductor.

Another embodiment of the present disclosure may include a memory card (e.g., a secure digital (SD) card, a subscriber identification module (SIM) card, etc.) including a capacitance sensor. More specifically, for example, a memory card may include moisture sense system 10 shown in FIG. 1. The memory card may be configured for being inserted into an electronic device. Thus, the memory card may enable an electronic device, which was previously unable to sense moisture, to sense moisture. It is noted that this embodiment may also include an application for interacting with the electronic device.

Figure 9:
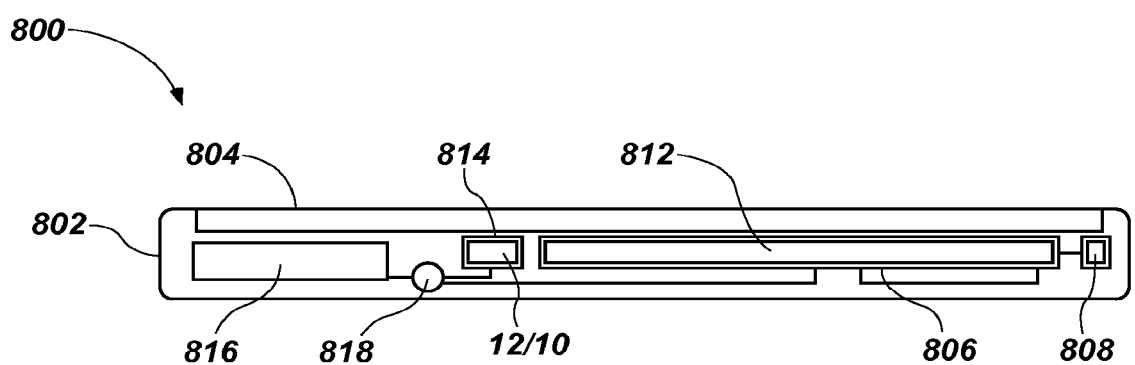
FIG. 9 schematically depicts an embodiment of an electronic device that includes a moisture sensor and, optionally, a moisture sense system.

FIG. 9 depicts an embodiment of an electronic device 800 that includes a moisture sensor 12, as well as a housing 802, a display 804, its primary electronic components (e.g., electronic components that enable the electronic device to function as intended, such as processors, wireless communication elements, input and/or output elements, transducers, etc.), and any other electronic and/or mechanical components. In some embodiments, such as that depicted by FIG. 9, the moisture sensor 12 is part of a moisture control system 10, such as that shown in FIG. 1.

The electronic device 800 may comprise a portable electronic device, an electronic device that is expected to be used in an environment where exposure to moisture is likely or even expected, or any of a variety of other types of electronic devices. The housing 802 and display 804 define at least part of an exterior of the electronic device 800. The moisture sensor 12 may, in some embodiments, be located at or at least exposed to the exterior of the electronic device 800. In other embodiments, the moisture sensor 12 may be located within an interior of the electronic device 800, along with other components of the moisture control system 10 (FIG. 1), if any, the primary electronic components of the electronic device 800, and a power supply 816, which provides power to various electronic components of the electronic device 800. Without limitation, the primary electronic components of the electronic device may include a processing element 806 (e.g., microprocessor, etc.), a wireless communication system 808 (which may include at least one antenna), and other electronic and/or mechanical components 812 (e.g., transducers, such as speakers, microphones, etc.; vibrators; fans; etc.). In the illustrated embodiment, a switch 818 is disposed between the power supply 816 and the primary electronic components, and between the power supply 816 and the moisture sensor 12 and any other components of the moisture sense system 10.

In some embodiments, the electronic device 800 may also include one or more moisture-resistant coatings 814. A moisture-resistant coating 814 may cover all or part of an exterior of the electronic device 800, all or part of surfaces that are internally confined within the electronic device 800 (e.g., surfaces of components or combinations of components within the interior of the electronic device 800, etc.), or both external and internal surfaces.

Various embodiments of methods for sensing and responding to exposure of an electronic device 800 to an amount of moisture that meets or exceeds a moisture event threshold (e.g., a predetermined, unsafe level of moisture, such as 95% relative humidity or greater, exposure to water or another electrically conductive material in liquid form, etc.) may include sensing an amount of moisture to which the electronic device is exposed (e.g., with a moisture sensor 12, etc.). Sensing may occur continuously or periodically. If the amount of moisture detected (e.g., by the moisture sensor 12, etc.) meets or exceeds the moisture event threshold, a normal operational mode of the electronic device 800 may be terminated, and a moisture event mode of the electronic device 800 may be initiated.

As the electronic device 800 exits its normal operational mode, the supply of power from a power supply 816 to one or more electronic components of the electronic device 800 may be terminated. The moisture event mode of an electronic device 800 may interrupt charging of a power source of the electronic device 800. In some embodiments, this moisture event mode of the electronic device 800 may include a complete shut-down of the electronic device 800. In other embodiments, the moisture event mode of the electronic device 800 may comprise a safe mode, in which certain components (e.g., primary electronic components that have been made moisture resistant, components that are unlikely to fail when exposed to moisture, etc.) of the electronic device 800 may continue to operate. In some embodiments, operation of the device in the safe mode may enable the moisture sensor 12 or other components of the moisture sense system 10, if any, to continue operation, while the communication of power from the power supply 816 to any primary electronic components that do not participate in the moisture sense system may be terminated.

As an electronic device 800 enters the safe mode, or moisture event mode, the electronic device 800 or a moisture sense system 10 associated with the electronic device 800 may generate a notification. The notification may include a user-perceptible warning, the generation and transmittal of a signal to a remote monitoring service or a combination of these services. Without limitation, a remote monitoring service may include the manufacturer, vendor or an owner or user of the electronic device, a party that has been engaged to monitor, update, service or repair the electronic device, a party that provides warranty coverage for or insures the electronic device, or any other suitable party.

A user-perceptible warning may be provided by a physical indicator (e.g., sight, sound, motion, etc.) on the electronic device. Alternatively, a warning may be remotely transmitted to a user or a monitoring service (e.g., as a text message, an e-mail, an instant message, a telephone call, or any other suitable form of automated electronic communication). Such a warning may merely indicate that a particular electronic device has been exposed to moisture, or it may include other information, such as information about the time at which the electronic device was exposed to moisture, the type of moisture to which the electronic device has been exposed, the extent of exposure, the duration of the exposure, the number of times the electronic device has been exposed to moisture (i.e., a tally), the cumulative duration of exposure of the electronic device to moisture, the geographic location of the electronic device at the time of exposure, warranty information, contact information for the user and/or owner of the electronic device, information on any prior exposure of the electronic device to moisture, and any other relevant information about exposure of the electronic device to moisture. With such information, the recipient may use the information themselves or assist the user of the electronic device, record the information that has been received, and/or schedule a reminder to follow up with the user.

In embodiments where moisture monitoring continues while an electronic device 800 is in moisture event mode, the electronic device 800 may be allowed to resume full operation once an acceptable level of moisture (e.g., a predetermined reset threshold, an amount of moisture below a predetermined moisture event threshold, etc.) is detected. In such an embodiment, when the amount of moisture detected drops to or below a predetermined reset threshold, a predetermined moisture event threshold, or any other suitable reset condition or combination of reset conditions have been met, the moisture event mode of the electronic device 800 may be exited, and the normal operational mode of the electronic device 800 may resume. Resumption of normal, or full, operation of the electronic device 800 may be automatic upon occurrence of the reset condition(s), or resetting of the electronic device 800 may occur when an individual (e.g., a user, an administrator, etc.) causes normal operation of the electronic device 30 to resume (e.g., following an inspection, etc.).

A moisture sensor comprised of one or more of an inductive sensor, capacitive sensor, accelerometer (to register dropping or throwing of a device), optical sensor (e.g. onboard camera, infrared emitter/sensor pair), piezo sensor, microphone, speaker (utilized as a pressure gauge), conductivity sensor, temperature sensor, humidity sensor (e.g. mechanical, electrical, gel), a sacrificial or fuse-like element which interrupts circuit connectivity with the presence of moisture beyond a specific threshold, wireless communication circuitry (e.g. GPS receiver circuits, WIFI and Bluetooth transceiver circuits, cellular telephone transceiver circuits, antennas). Any of these devices can be used together with control circuitry to apply Boolean logic to one or more trigger events detected by the sensory devices. The quality and material properties of the moisture event will be ascertained by using one or more of the aforementioned devices jointly or in a Boolean arrangement together with the control circuitry.

Although the foregoing description contains many specifics, these should not be construed as limiting the scope of any of the appended claims, but merely as providing information pertinent to some specific embodiments that may fall within the scopes of the appended claims. Features from different embodiments may be employed in combination. In addition, other embodiments may also be devised which lie within the scopes of the appended claims. The scope of each claim is, therefore, indicated and limited only by its plain language and the legal equivalents to the recited elements. All additions, deletions and modifications to the disclosed subject matter that fall within the meaning and scopes of the claims are to be embraced by the claims.

What is claimed:

1. An electronic device, comprising: a housing and a display defining an exterior of an electronic device and an interior of the electronic device; an integrated circuit (IC) within the electronic device and comprising a control element; and a moisture sensor comprising at least one inductive sensor, the moisture sensor being coupled to or part of the IC and associated with the control element, the moisture sensor and the control element together being configured to sense moisture within the electronic device, wherein the at least one inductive sensor is configured to generate a magnetic field and detect a change in magnetic permeability, the inductive sensor including an inductive coil surrounding the IC and configured to receive a voltage pulse from the IC.

2. The electronic device of claim 1, further comprising an oscillator configured to convey a clock signal to the moisture sensor and the control element.

3. The electronic device of claim 1, wherein the control element is programmable via a communications port of the IC.

4. The electronic device of claim 1, the moisture sensor comprising a capacitance sensor including a shield surrounding a sense element and separated from the sense element by an air gap.

5. The electronic device of claim 1, wherein the control element includes one or more logic circuits.

6. The electronic device of claim 1, the IC configured to measure an electrical current response after conveying the voltage pulse to determine if moisture is present proximate the IC.

7. The electronic device of claim 1, further comprising a ball grid array (BGA) package including the inductive sensor.

8. The electronic device of claim 1, further comprising at least one moisture-resistant element coating at least a portion of the moisture sensor.

9. A system, comprising: an integrated circuit (IC) comprising a processing element and logic calibrated for determining an occurrence of a moisture event based on a received sensor signal; and a moisture sensor comprising at least one inductive sensor coupled to the processing element and configured to generate a magnetic field and detect a change in magnetic permeability and convey the sensor signal to the logic, the sensor signal indicative of a measured magnetic permeability proximate the moisture sensor, the inductive sensor including an inductive coil surrounding the IC and configured to receive a voltage pulse from the IC.

10. The system of claim 9, the inductive sensor internal to the IC and configured to detect moisture proximate the IC.

11. The system of claim 9, the system further including a shield and a sense element external from and coupled to the IC.

12. The system of claim 11, the shield surrounding the sense element, wherein the inductive sensor is configured to detect moisture within a gap separating the shield and the sense element.

13. The system of claim 11, wherein the shield is coupled to a ground voltage.

14. The system of claim 9, the inductive sensor configured to receive a clock signal from an oscillator.

15. A method for responding to exposure of an electronic device to moisture, comprising: measuring a change in magnetic permeability within the electronic device, with at least one inductive sensor, the inductive sensor including an inductive coil; receiving a voltage pulse, at the inductive coil, from an integrated circuit (IC); determining if moisture is within the electronic device based on the measured change in magnetic permeability; and entering a moisture sense mode of the electronic device if it is determined that moisture is within the electronic device.

16. The method of claim 15, further comprising measuring a change in dielectric constant within the electronic device with at least one capacitance sensor.

17. The method of claim 15, further comprising calibrating one or more moisture event thresholds of the electronic device based on one or more conditions.

* * * * *